(12) United States Patent
Liang

(10) Patent No.: US 10,893,798 B2
(45) Date of Patent: Jan. 19, 2021

(54) METHODS AND SYSTEMS FOR UPDATING REFRACTIVE PRESCRIPTIONS AND DELIVERING EYEGLASSES AND CONTACT LENSES

(71) Applicants: PERFECT VISION TECHNOLOGY (HK) LTD., Tsuen Wan (HK); Junzhong Liang, Fremont, CA (US)

(72) Inventor: Junzhong Liang, Fremont, CA (US)

(73) Assignee: PERFECT VISION TECHNOLOGY (HK) LTD., Tsuen Wan (HK)

( * ) Notice: Subject to any disclaimer, the term of this patent is extended or adjusted under 35 U.S.C. 154(b) by 174 days.

(21) Appl. No.: 16/321,422

(22) PCT Filed: Aug. 9, 2016

(86) PCT No.: PCT/US2016/046212
§ 371 (c)(1),
(2) Date: Jan. 28, 2019

(87) PCT Pub. No.: WO2018/031001
PCT Pub. Date: Feb. 15, 2018

(65) Prior Publication Data
US 2019/0335993 A1    Nov. 7, 2019

(51) Int. Cl.
*A61B 3/103*    (2006.01)
*A61B 3/028*    (2006.01)
(Continued)

(52) U.S. Cl.
CPC .............. *A61B 3/103* (2013.01); *A61B 3/028* (2013.01); *A61B 3/032* (2013.01); *A61B 3/107* (2013.01)

(58) Field of Classification Search
CPC .......... A61B 3/14; A61B 3/0025; A61B 3/12; A61B 3/102; A61B 3/0058
(Continued)

(56) References Cited

U.S. PATENT DOCUMENTS 6,386,707 B1    5/2002  Pellicano
10,444,539 B2 *  10/2019  Liang ..................... G02C 7/027
(Continued)

FOREIGN PATENT DOCUMENTS

WO    2014085352 A1    6/2014

OTHER PUBLICATIONS

International Search Report and Written Opinion dated May 8, 2017 for PCT Patent Application No. PCT/US2016/046212.

*Primary Examiner* — Mohammed A Hasan
(74) *Attorney, Agent, or Firm* — MLO, a professional corp.

(57) ABSTRACT

Methods and systems for producing a refractive prescription for a consumer away from an optical office are disclosed. At a first time point, a first prescription for a first pair of corrective lenses is generated according to measured refractive errors, and a historical visual acuity profile is measured using the first prescription and a varying spherical power. At a second time point, a second visual acuity is measured using the first prescription. A new spherical power is computed using the historical visual acuity profile and the second visual acuity. A second prescription for a second pair of corrective lenses is generated based on the first prescription and the new spherical power. In some embodiments, the second visual acuity may be self-administered by the consumer away from an optical office.

42 Claims, 6 Drawing Sheets

(51) Int. Cl.
    *A61B 3/032* (2006.01)
    *A61B 3/107* (2006.01)
(58) Field of Classification Search
    USPC .......................................................... 351/206
    See application file for complete search history.

(56) References Cited

U.S. PATENT DOCUMENTS

| | | | |
|---|---|---|---|
| 2006/0264917 A1* | 11/2006 | Tuan | G02C 7/048 606/5 |
| 2013/0188143 A1 | 7/2013 | Carmon et al. | |
| 2015/0070650 A1 | 3/2015 | Seriani | |
| 2016/0128560 A1 | 5/2016 | Lee et al. | |

* cited by examiner

METHODS AND SYSTEMS FOR UPDATING REFRACTIVE PRESCRIPTIONS AND DELIVERING EYEGLASSES AND CONTACT LENSES

BACKGROUND

Obtaining eyeglasses or contact lenses for vision correction of human eyes typically involves patients or consumers visiting ophthalmologist offices, optometrist offices, or eyeglass shops.

People often receive a new pair of eyeglasses every couple of years because of vision degradation over time, damage to the eyeglasses (frame or lenses), or the need to change the look of the eyeglasses. When people replace their eyeglasses, they still need to visit a professional office in order to get an updated prescription for various reasons. For example, an eye's optics can change from the last office visit so that the eyes must be reexamined in order to get an up-to-date prescription. Also, the refractive prescription is subjective and an eyeglass or contact prescription of the same patient (consumer) can be different from office to office, and even different from optometrist to optometrist within the same office. Consumers usually get another chance to get their eyes examined by another professional, and hope to improve their vision correction. Another reason to visit a professional optical office to update a lens prescription is that as people age and have presbyopia, their vision prescription also depends on the amount of presbyopia in the eyes as well as the person's lifestyle.

Autorefractors have been around for more than thirty years, and aberrometers have been around for more than ten years. Efforts have been made recently to convert smart phones or home computers to an autorefractor or an aberrometer so that people can perform refraction at home. However, even though autorefractors and aberrometers are available at optometry offices or at home, getting prescriptions for corrective lenses still needs to be administrated by experienced professionals.

Consequently, although many configurations and methods for vision correction are known in the art, they suffer from one or more disadvantages. Thus, there is a need to improve methods and systems for updating refractive prescriptions and delivering eyeglasses or contact lenses to consumers.

SUMMARY

In some embodiments, a method for producing a refractive prescription for human eyes includes using a refraction device to obtain measured refractive errors of eyes of a tested subject at a first time point. A first prescription for a pair of corrective lenses is generated according to the measured refractive errors, the first prescription including a spherical power fs1 and if applicable, a cylinder power fc1 and a cylinder angle fa1. At a first time point, a historical visual acuity profile Va($\Delta$fs) of the eyes of the tested subject is measured. The historical visual acuity profile Va($\Delta$fs) comprises a plurality of visual acuities Va(i) that are measured using the spherical power fs1 of the first prescription, with a plurality of variations in spherical power $\Delta$fs(i). The historical visual acuity profile Va($\Delta$fs) and data on the first prescription are recorded. At a second time point, a second visual acuity Va2 of the eyes of the tested subject is measured using the pair of corrective lenses according to the first prescription. A new spherical power fs2 for the eyes of the tested subject is computed using the historical visual acuity profile Va($\Delta$fs) and the second visual acuity Va2. A second prescription for a second pair of corrective lenses is generated based on the first prescription and the new spherical power for the eyes, the second prescription comprising the spherical power fs2 and if applicable, the cylinder power fc1 and the cylinder angle fa1.

In other embodiments, a method for updating a refractive prescription for human eyes includes receiving current information of eyes of a tested subject. The current information includes a) identification information of current corrective lenses of the tested subject, the identification information assigned at a first location, such as by a lens vendor, and b) a current visual acuity VAc for each eye of the tested subject with the current corrective lenses, the current visual acuity VAc being assessed at a second location, such as away from the lens vendor. The identification information of the current corrective lenses is used to retrieve historical data. The historical data includes I) a historical prescription comprising a spherical power fs1 for the current corrective lenses, and if applicable, a cylinder power fc1 and a cylinder angle fa1. The historical data also includes II) a historical visual acuity profile Va($\Delta$fs) describing a relationship between a plurality of measured visual acuities Va(i) and a plurality of variation in spherical power $\Delta$fs(i) on top of the historical prescription. A new spherical power fs2 is computed based on the current visual acuity VAc and the historical visual acuity profile Va($\Delta$fs). A new prescription for a new pair of corrective lenses is generated, where the new prescription includes the new spherical power fs2 and if applicable, the cylinder power fc1 and the cylinder angle fa1.

In yet other embodiments, a system for producing a refractive prescription of corrective lenses includes a storage module, an input module, a computer module and an output module. The storage module is configured to store I) a first prescription for a first pair of corrective lenses, where the first prescription comprises a spherical power fs1 and if applicable, the cylinder power fc1 and the cylinder angle fa1. The storage module is also configured to store II) a historical visual acuity profile Va($\Delta$fs) that describes a relationship between a measured visual acuity Va(i) and a variation in spherical power $\Delta$fs(i), the historical visual acuity profile Va($\Delta$fs) being measured at a first time point. The input module is configured to receive a second visual acuity Va2 of the eyes of the tested subject, the second visual acuity Va2 being measured at a second time point using the first prescription or the first pair of corrective lenses according to the first prescription. The computer module is configured to a) retrieve the first prescription from the storage module, b) compute a new spherical power of the eyes of the tested subject based on the historical visual acuity profile Va($\Delta$fs) and the second visual acuity Va2, and c) generate a second prescription for a second pair of corrective lenses based on the first prescription and the computed new spherical power of the eyes. The output module is configured to export the second prescription.

In other embodiments, a refraction system for producing a refractive prescription of corrective lenses includes a refraction module, an acuity profile module, and an output module. The refraction module is configured to measure refractive errors in left and right eyes of a tested subject and to generate a prescription for a pair of corrective lenses with which both left and right eyes of the tested subject are corrected for the best vision performance. The acuity profile module is configured to measure and record a plurality of visual acuities of the left and right eyes of the tested subject as a function of spherical power, the measuring comprising changing a spherical power setting of the refraction module and recording each visual acuity at each spherical power setting based on feedback from the tested subject. The plurality of visual acuities forms an acuity profile. The output module is configured for 1) printing, displaying, and exporting the generated prescription for the pair of corrective lenses, and 2) printing, displaying, and exporting the acuity profile.

In still other embodiments, a method for producing a refractive prescription of corrective lenses includes determining, at a first time point, a first prescription of a first pair of corrective lenses worn by a tested subject. The determining is based on a record of a previous prescription or using a lensometer to measure the first pair of corrective lenses. The first prescription includes a spherical power fs1 and if applicable, a cylinder power fc1 and a cylinder angle fa1. A first visual acuity profile Va($\Delta$fs) of each eye of the tested subject is measured at the first time point, the first visual acuity profile comprising a plurality of measured visual acuities Va(i) measured using the first prescription with a plurality of the variations in spherical power $\Delta$fs(i). The first visual acuity profile Va($\Delta$fs) is recorded, where the first visual acuity profile Va($\Delta$fs) describes a relationship between the measured visual acuities Va(i) and the variation in spherical power $\Delta$fs(i). A new prescription of corrective lenses for the tested subject at a second time point later than the first time point is generated, using the first visual acuity profile Va($\Delta$fs).

In other embodiments, a method for updating a prescription of corrective lenses includes using, at a first time point, a conventional method in an optical office to obtain a first pair of corrective lenses for eyes of a tested subject. The following information is collected: a) a first prescription of the first pair of corrective lenses, and b) vision performance of the eyes that is measured with the first pair of corrective lenses plus a plurality of variations in spherical power $\Delta$fs(i). At a second time point, a visual acuity Va2 of the eyes is collected with the first pair of corrective lenses by non-optically trained person at a location away from any optical office when the new pair of corrective lenses is ordered away from any optical office. A change in spherical power of each eye from the first time point to the second time point is determined. A second prescription for a second pair of corrective lenses is generated based on the information collected at the optical office and the visual acuity Va2.

In further embodiments, a method for updating a prescription of corrective lenses includes using a conventional method in an optical office to obtain a first pair of corrective lenses for eyes of a tested subject. The following information is collected: a) the first prescription of the first pair of corrective lenses, and b) a first visual performance of the eyes, the first visual performance comprising a visual acuity profile Va($\Delta$fs) of the eyes with the first pair of corrective lenses. The conventional method uses a refraction device to measure refractive errors of both left and right eyes of the tested subject. A second visual performance of the eyes is collected, comprising a second visual acuity Va2 with the first pair of corrective lenses by self-administration away from any optical office. The collecting of the second visual performance is performed for a plurality of variations in spherical power $\Delta$fs(i) by i) measuring acuity through lenses and the first pair of corrective lenses or ii) placing acuity chart at a plurality of distances. A new prescription for a new pair of corrective lenses is generated based on the information collected at the optical office and the second visual performance collected with the first pair of corrective lenses away from any optical office.

DETAILED DESCRIPTION

Figure 1:
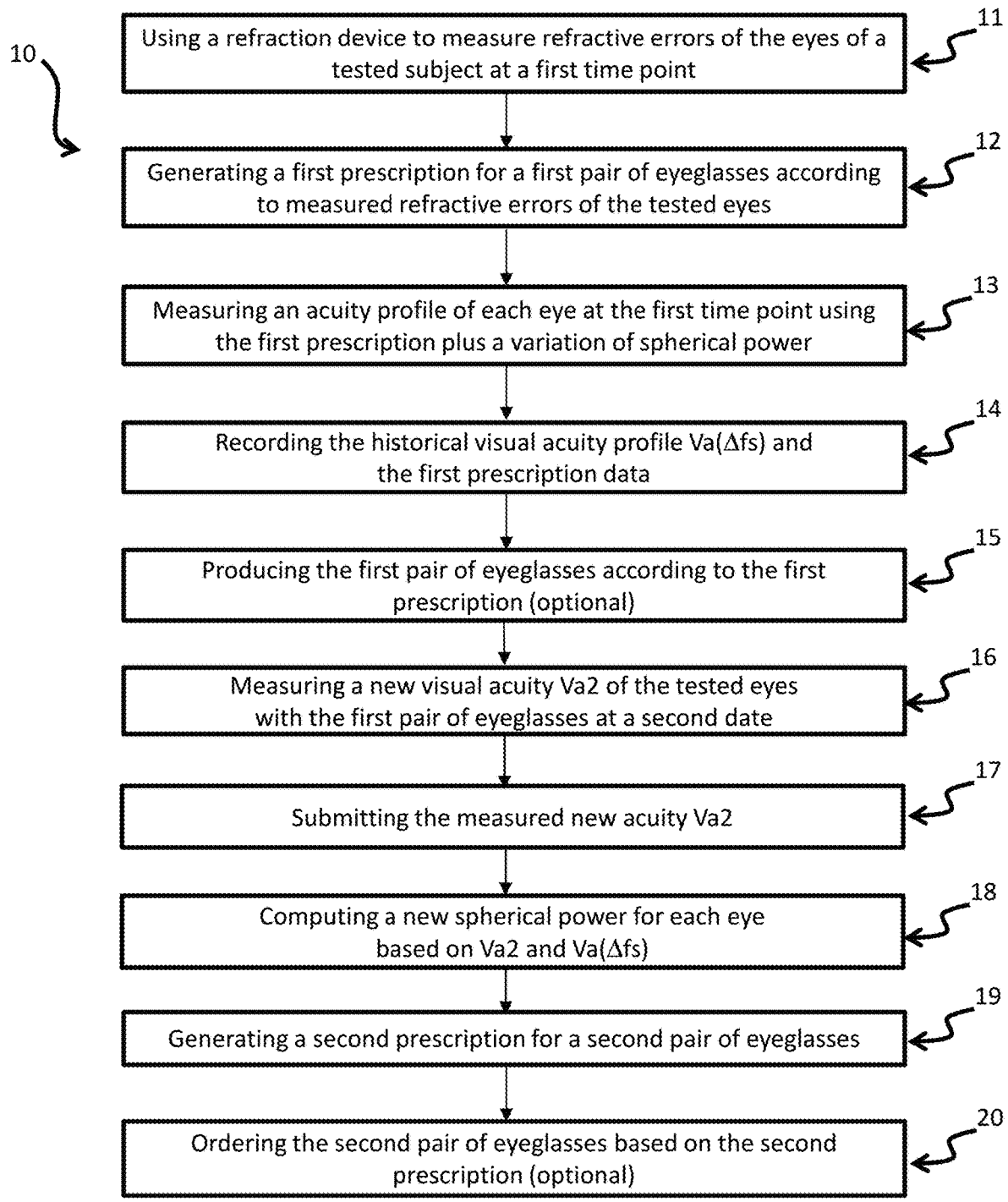
FIG. 1 shows a flow chart of a method to generate a refractive prescription of corrective lenses in accordance with some embodiments, using measurements from a first date to generate a refractive prescription at a later date without the need for an optical office.

It is almost impossible to determine prescriptions of eyeglasses or contact lenses for human eyes by consumers at home as reliably as in eyeglass shops by professionals for a number reasons. First, it is presently not possible to measure optical defects in eyes of tested subjects accurately with home electronics. Second, people must get a suitable prescription of eyeglasses that does not have problems such as lens distortion by the eyeglasses, and lens adaptation with new biocular vision corrections. These problems are much more difficult to overcome away from an optometry office.

The present disclosure describes methods and systems for determining refractive prescriptions and delivering eyeglasses or contact lenses away from an optical office, with the same or equivalent precision and reliability as would be achieved in a professional office. Using a first prescription determined by an optical professional such as an optometrist or ophthalmologist, a consumer may generate a second prescription at a later time point without the need for visiting a professional office. The methods and systems utilize a baseline visual acuity profile along with the first prescription to predict or generate the later prescription. The consumer is thus able to use the second prescription to order eyeglasses and contact lenses and have them delivered without the need for an optical professional.

In this disclosure, references to corrective lenses shall include eyeglasses or contact lenses. Similarly, although some embodiments may be described in terms of eyeglasses, they may also apply to contact lenses. The term spherical power is the amount of power in a prescription for the focus power or focus error of an eye. Accordingly, descriptions of variations in spherical power and spherical power settings may also be referred to as variations in focus power settings or focus settings. References to an optical professional shall refer to, for example, an optometrist, ophthalmologist, or a person having professional training in optical matters such as refractive measurements and prescribing eyeglasses or contact lenses. An optical office shall refer to a site designated for offering optical services regarding measurements and prescriptions for vision correction, such as an ophthalmologist office, an optometry service, or an eyeglass shop or lens vendor.

In various embodiments, a three-step solution addresses the issues of refraction at home or at a location other than at an optical office. The methods involve steps for producing refractive prescriptions and also include the corresponding information processing for those steps. First, an initial pair of corrective lenses such as eyeglasses for a tested subject (consumer) must be prescribed in an optical office such as an eyeglass shop, so that quality of the vision correction is not compromised. In addition to obtaining the first prescription of the eyeglasses in a conventional process, vision performance of the eyes is measured with the first pair of eyeglasses using a plurality of different focus settings. This measurement of vision performance with the first pair of eyeglasses through focus settings, by varying spherical power, can be used for the prediction of visual performance of the eyes if their spherical power is changed in the future.

Second, visual performance of the tested subject with the first pair of eyeglasses is assessed again at a later time point when a new pair of eyeglasses is required, which can be performed by the tested subject independently from an optical office.

Third, using the updated vision performance of the eyes with the first pair of eyeglasses as well as the predicted visual performance of the same eyes with the first eyeglasses stored in a historical file, one can determine the change in spherical power of each eye from the time of the first eyeglasses to the later time point. For example, the later time point may be the present date at which the consumer wishes to have the new eyeglasses made. The new prescription of eyeglasses can be determined by adding the determined change in spherical power of each eye to the prescription of the first pair of eyeglasses. Once a new pair of eyeglasses is received, the consumer can verify its performance. This verification can occur, for example, by the consumer wearing the new eyeglasses and deciding whether the prescription provides acceptable vision performance. In rare cases if the tested subject has issues with the new pair of eyeglasses because aberrations in the eyes may have changed over time, the subject can go to an eyeglass shop or other optical office to have their eyes re-examined.

FIG. 1 shows a flow chart 10 of a method for producing refractive prescription of eyeglasses for human eyes that enables a consumer to use a baseline prescription to determine an updated prescription for a new pair of eyeglasses away from conventional optometry offices or eyeglass shops in the future, according to some embodiments. In step 11, a refraction device is used to measure refractive errors of both left and right eyes of a tested subject at a first time point. The refraction device may include, for example, a phoropter and/or an aberrometer. The measurements using the refraction device at the first time point is administered by an optical professional at a first optical office. In one embodiment, the cylinder power fc1 and cylinder angle fa1 are objectively determined by taking measurements with an aberrometer, and the spherical power is subjectively determined by the tested subject with a professional. That is, using the refraction device can include measuring aberrations in the eyes with objective measurements from an aberrometer, the objective measurements comprising a cylinder power fc1 and a cylinder angle fa1; and measuring, by an optical professional, a spherical power of the eyes with subjective responses from the tested subject. The subjective measurements may include, for example, subjective responses from the tested subject to a plurality of variations in spherical power on a phoropter. Using the measurements of step 11, a first prescription for a pair of eyeglasses is generated in step 12. The first prescription of a pair of eyeglasses includes at least a focus error (spherical power) fs1, and optionally a cylinder angle fc1 and a cylinder angle fa1. That is, in some embodiments the measured refractive errors in generating the first prescription comprises the cylinder power fc1, the cylinder angle fa1, and the spherical power fs1 for each eye. The cylinder power fc1 and cylinder fa1 are included in the first prescription if applicable; in other words, if they have a non-zero value. The first prescription may further address coma and spherical aberration in the eyes as measured by the aberrometer.

Next, step 13 involves measuring an acuity profile using the generated prescription of eyeglasses. The acuity profile is performed through focus; that is, by changing only the focus/spherical power. The acuity profile includes a plurality of visual acuities (Va(1), Va(2), ... Va(i)) that are measured by having the tested subject evaluate vision using the first prescription plus adding a plurality of variations ($\Delta$fs(1), $\Delta$fs(2), ... $\Delta$fs(i)) to the spherical power fs1, where the variations may be towards more myopic. The acuity profile is a historical visual acuity profile Va($\Delta$fs) of the eyes of the tested subject, where the historical visual acuity profile Va($\Delta$fs) comprises the plurality of visual acuities Va(i) measured using the first prescription with a plurality of variations in spherical power $\Delta$fs(i) from the spherical power fs1 of the first prescription. The resulting visual acuity profile Va($\Delta$fs) describes the relationship between the measured visual acuity Va(i) and the variation in spherical power $\Delta$fs(i), and is recorded as a historical visual acuity profile Va($\Delta$fs) in step 14. The first prescription data is also recorded in the historical record or file, such as the values of the spherical power fs1, cylinder angle fa1 and cylinder power fc1. The first prescription may also include a correction for spherical aberration or coma, in some embodiments. The acuity profile and data about the first prescription may recorded, for example, in a written record, an electronic database of the optical office, or a web- or cloud-based file. In some embodiments, a pair of eyeglasses is produced in step 15 and delivered to the tested subject according to the first prescription. The first prescription as well as the acuity profile are obtained by a professional at an optical office at the first time point.

In step 16, a new (i.e., second) visual acuity Va2 of the eyes of the tested subject are measured at a second time point after the first time point, using the first pair of corrective lenses (e.g., eyeglasses) that are according to the first prescription. The second time point occurs at a time when the patient needs an updated prescription from the previous prescription, such as half a year, a year, or two years later after the first time point. These measurements can be administrated by a non-optically trained person at a location away from an optical office. For example, the new visual acuity Va2 can be self-administered by the tested subject away from an optical office and possibly at home on the later date. In some embodiments, the new visual acuities Va2 can be administered by a non-optically trained person. For example, the tested subject may utilize a friend, who does not have professional training as an optician, to assist with the measurements. The measured new acuity Va2 is submitted in step 17. A new spherical power fs2 for each eye is computed in step 18 using the recorded historical visual acuity profile Va($\Delta$fs) and the second visual acuity Va2 submitted by the tested subject in step 17 at the second time point. The computing may involve retrieving the historical visual acuity profile Va($\Delta$fs) from a web-based or cloud-based system. A second prescription for a second pair of corrective lenses (e.g., eyeglasses) is generated in step 19, based on the first prescription for the first pair of eyeglasses plus the new spherical power fs2 computed in step 18. The second prescription includes the spherical power fs2 and if applicable, the cylinder power fc1 and the cylinder angle fa1. Optionally, the method may also involve ordering and delivering the second pair of corrective lenses (e.g. eyeglasses) according to the second prescription in step 20, such as by ordering and delivering from a lens vendor. After the tested subject receives the lenses, the method may include verifying, by the tested subject, performance of the second pair of corrective lenses. The method in FIG. 1 can be further configured into a web-based, a cloud-based, or a remote system.

Measurement of the visual acuities of the tested eyes with the first pair of eyeglasses at home at a later time point, as in step 16 of FIG. 1, may involve placing an acuity chart at a plurality of distances from the tested subject. For example, the test subject has an acuity chart and set of test lenses of varying spherical powers, and reads the chart using the test lenses. In some embodiments, the test of visual acuity at home is performed under a controlled environment for at least one factor such as light conditions, type of acuity chart, and distance from the acuity chart to the tested subject. In some embodiments, the measuring may also include determining an add-on spherical power for a presbyopia correction.

Figure 2A:
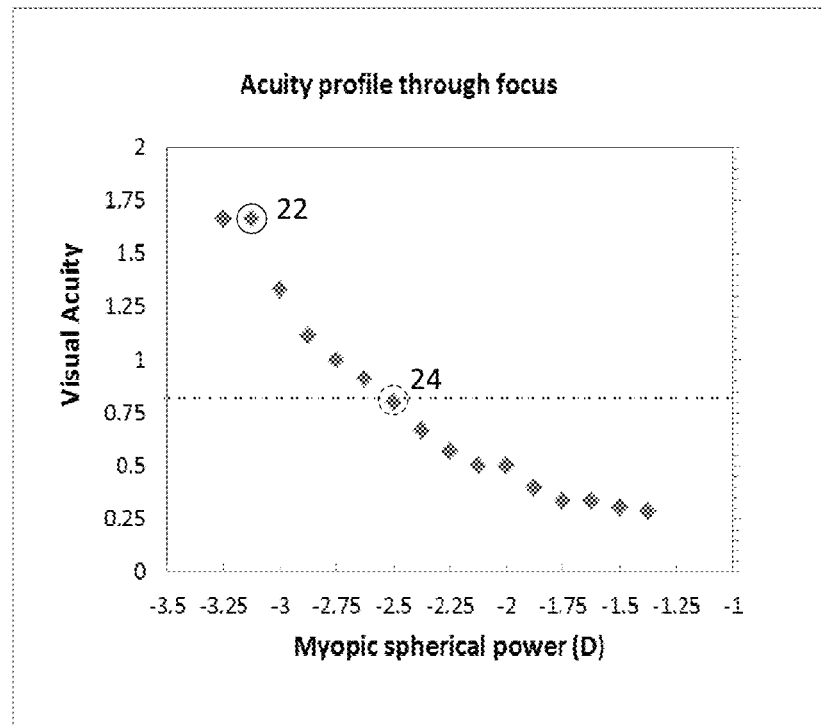
FIGS. 2*a*-2*b* show acuity profiles of an eye, measured using focus power variation when the eyeglasses were first prescribed.
Figure 2B:
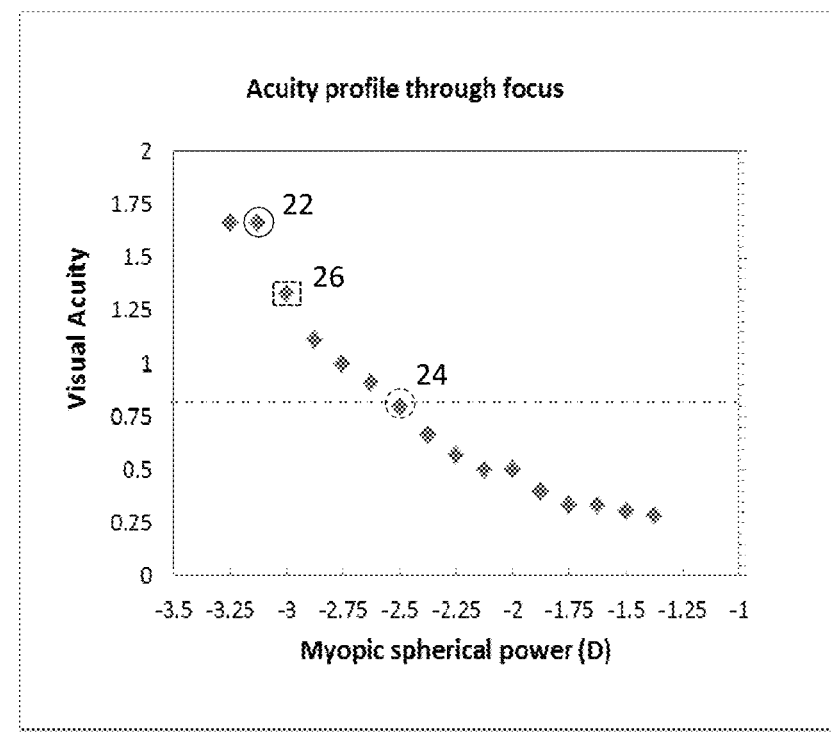

Examples of acuity profiles are shown in FIGS. 2a and 2b. FIG. 2a shows an exemplary acuity profile through focus of an eye when the eyeglasses were first prescribed. Each point in the graph is a measured visual acuity Va(i) in the acuity profile at a first time point. The tested eye has the best visual acuity of 20/12 for myopic power of −3.25D and −3.125D (diopters D). The spherical power fs1 (solid circle 22 in FIG. 2a) in the first prescription is thus −3.125D because it is the lowest myopic power at the best acuity of 20/12. As the eye becomes more myopic in the future, visual acuity of the tested eye will be gradually reduced depending on the new myopic power.

On a later date, visual performance of the tested subject with the first pair of eyeglasses is assessed again. Suppose the measured acuity is 20/25 with the first pair of eyeglasses on the second, later date. The acuity of 20/25 (dotted circle 24 in FIG. 2a) on the later date, which would then be considered as the present date, is placed onto the historical acuity profile, which thus shows that the tested eye with the first pair of eyeglasses becomes more myopic by −0.625D. If we add −0.625D to the original −3.125D to the first prescription, the eye at present should be restored to have acuity of 20/12. Therefore, by correlating the present acuity measurement with the historical acuity profile and the original prescription information, an updated prescription based on the first prescription is computed, with a new spherical power of −3.75D instead of −3.125D.

FIG. 2b demonstrates how the reliability of the estimate can be further improved by providing a plurality of spherical lenses along with the first pair of eyeglasses to the tested subject. Suppose the tested subject has a spherical lens of −0.5D at home. The tested subject can measure the current acuity not only with the first pair of eyeglasses but also by adding the −0.5D lens in front of the first pair of eyeglasses. The measured acuity through the eyeglasses plus a −0.5D lens is now 20/15. The tested acuity with the −0.5D lens (dotted square 26) as well as the acuity with the first pair of eyeglasses (dotted circle 24) are placed in the acuity profile shown in FIG. 2b. It can be seen in FIG. 2b that the corrected eye with the eyeglasses plus −0.5D lens (dotted square 26) is still myopic by −0.125D (difference in diopters from the solid circle 22). It is therefore concluded that 1) the eye with the first pair of eyeglasses has a myopic power of −0.625D, and 2) the estimation is reliable because the second measured acuity fits well with the historical acuity profile.

The tested eye can also become less myopic in the real practice. This problem can be addressed by measuring acuity with the first pair of eyeglasses with some positive lenses available to the subject at home, such as +0.5D and +0.75D. For hyperopic patients, the test of acuity profile should be performed for more hyperopic powers in the optical shops.

The present methods have a number of advantages. First, it does not compromise quality of the refractive prescription because it is built on the first rigorous eye examination as well as predicted visual performance assessed in advance. Second, excellent prescription of eyeglasses or contact lenses can be obtained away from eyeglass shops, such as at home, which saves time and money for the tested subjects compared to visiting an office. Time and effort is also saved for the examiner at eyeglass shops and other optical offices. Third, it provides a closed loop validation of the new eyeglasses, and thus prevents wrong prescriptions in case the eyes of the tested subject have more changes beyond a simple variation in spherical power. In one embodiment, refractive prescription of the first pair of eyeglasses can be obtained using the technologies of wavefront customized eyeglasses as described in U.S. Pat. No. 8,419,185 (Liang, "Methods and Devices for Refractive Correction of Eyes," which is hereby incorporated by reference) that not only allows obtaining high-precision customized eyeglasses based on 20/10 optics of navy pilots but also makes the refraction process independent of subjective skills of an operator such as an optometrist. In another embodiment, refractive prescription of the first pair of eyeglasses can be obtained using the technologies in U.S. patent application Ser. No. 15/151,491 (Liang, "Methods and Systems for Determining Refractive Corrections of Human Eyes for Eyeglasses," filed on May 11, 2016, which is hereby incorporated by reference) that solves the problem of eyeglass distortion without subjective skills of an operator such as an optometrist.

The new technologies of U.S. Pat. No. 8,419,185 and U.S. patent application Ser. No. 15/151,491 enable the best refractive prescription possible for eyes of the tested subjects to be obtained, independent of the skills of optometrists and opticians. This solves the problem of consumers needing to get another chance to get their vision corrected better with their old eyeglasses and their prescription examined by another professional.

Figure 3:
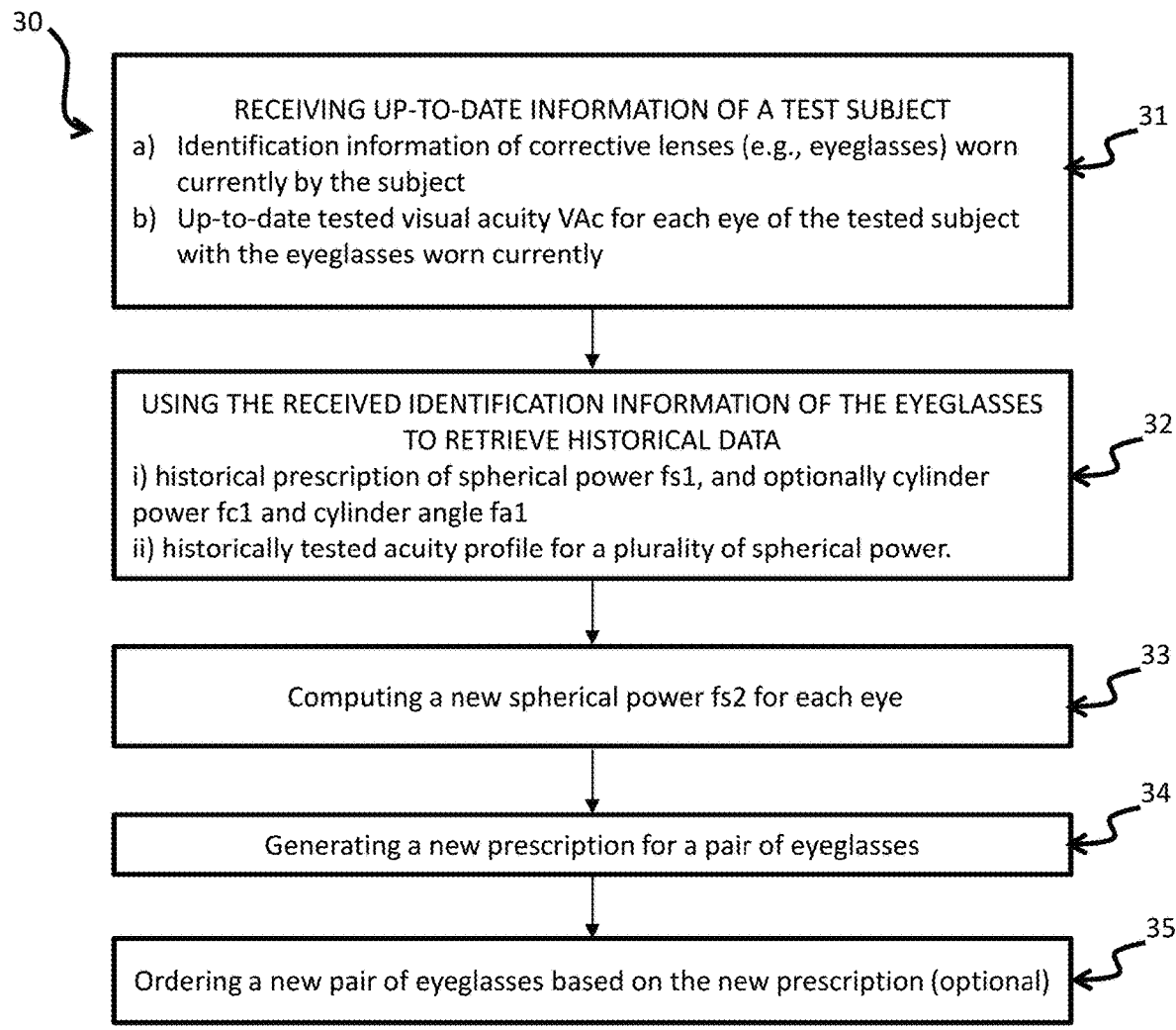
FIG. 3 shows a flow chart of a method for generating an updated prescription in accordance with some embodiments, based on an acuity profile measured with corrective lenses worn currently, historical prescription data, and historical acuity profile saved in a record.

FIG. 3 shows another embodiment of the present disclosure, in a flow chart 30 of a method for generating an updated prescription for a new pair of eyeglasses using a pair of lenses worn by a consumer at a present time point, and prior vision information of the consumer. More specifically, the method for updating a refractive prescription is based on acuity measured with eyeglasses worn currently, and its historical prescription, and a saved historical acuity profile of the eyes tested with the current eyeglasses. First, current (i.e., up-to-date for the present time point) information of eyes of a test subject is received in step 31 that includes a) the identification information of current corrective lenses of the tested subject, or an existing prescription for the tested subject and b) a current visual acuity VAc for each eye of the tested subject with the current corrective lenses. The identification information is assigned at a first location, such as by a lens or eyeglass vendor, where the identification information may be, for example, a serial number or identification code. The current visual acuity VAc is assessed at a location away from the lens vendor, such as at a second location different from the first location.

In step 32, historical data on the eyeglasses worn currently are retrieved from a database or stored file using the received identification information of the eyeglasses worn by the consumer. The historical data includes i) the historical prescription for the current corrective lenses (i.e., eyeglasses currently worn), which includes at least a spherical power fs1, and possibly a cylinder power fc1 and a cylinder angle fa1 if applicable; and ii) the historical visual acuity profile Va($\Delta$fs). The historical visual acuity profile Va($\Delta$fs) describes a relationship between a plurality of measured visual acuities Va(i) and a plurality of variation in spherical power $\Delta$fs(i) on top of the historical prescription. For example, the historical visual acuity profile Va($\Delta$fs) includes a plurality of visual acuities Va(i) of the eyes measured using the historical prescription and a plurality of variations of the historical prescription varying only in the spherical power $\Delta$fs(i). In step 33, a new spherical power fs2 for each eye is computed based on the received up-to-date tested visual acuity VAc and the historically tested acuity profile Va($\Delta$fs). In step 34, a new prescription for a pair of new pair of corrective lenses, is generated. The new prescription includes the computed new spherical power fs2, and possibly a cylinder power fc1 and a cylinder angle fa1 from the historical prescription value for the eyeglasses currently worn. In step 35 according to one embodiment, a new pair of eyeglasses is ordered and delivered based on the new prescription.

In one embodiment, the eyeglasses worn currently by the subject is custom-made and its historical prescription includes a spherical power fs1, a cylinder power fc1 and a cylinder angle fa1 measured by an aberrometer, and possibly spherical aberration or coma in the tested eye measured by an aberrometer.

In one embodiment, the method in FIG. 3 is further configured into a web-based system, and even a cloud-based system. The web-based or cloud-based system may be accessible by a personal electronic device of the tested subject, where the personal electronic device may be, for example, personal computer, a laptop, a tablet, a smart phone, or a smart watch. In some embodiments, the receiving of up-to-date information of a test subject in step 31 is configured to obtain electronic records from the personal electronic device of the tested subject or to allow an operator to enter data provided by the tested subject. In some embodiments, the web-based or cloud-based system includes an input module configured to receive the historical data, a storage module configured to store the historical data received by the input module, and a computer module configured to compute the new spherical power fs2 and to generate the new prescription using the historical data stored on the storage module.

In one embodiment of the method in FIG. 3, the received up-to-date tested visual acuity VAc for each eye of the tested subject with the eyeglasses worn currently further includes a plurality of visual acuities measured with a test acuity chart placed at a plurality of distances for determining an add-on spherical power for a presbyopia correction.

In one embodiment of FIG. 3, the ordering and delivering of eyeglasses further includes accepting payment information from the tested subject, receiving delivery information from the individual (tested subject), and offering to and receiving from the individual a frame style for the new pair of eyeglasses.

Figure 4:
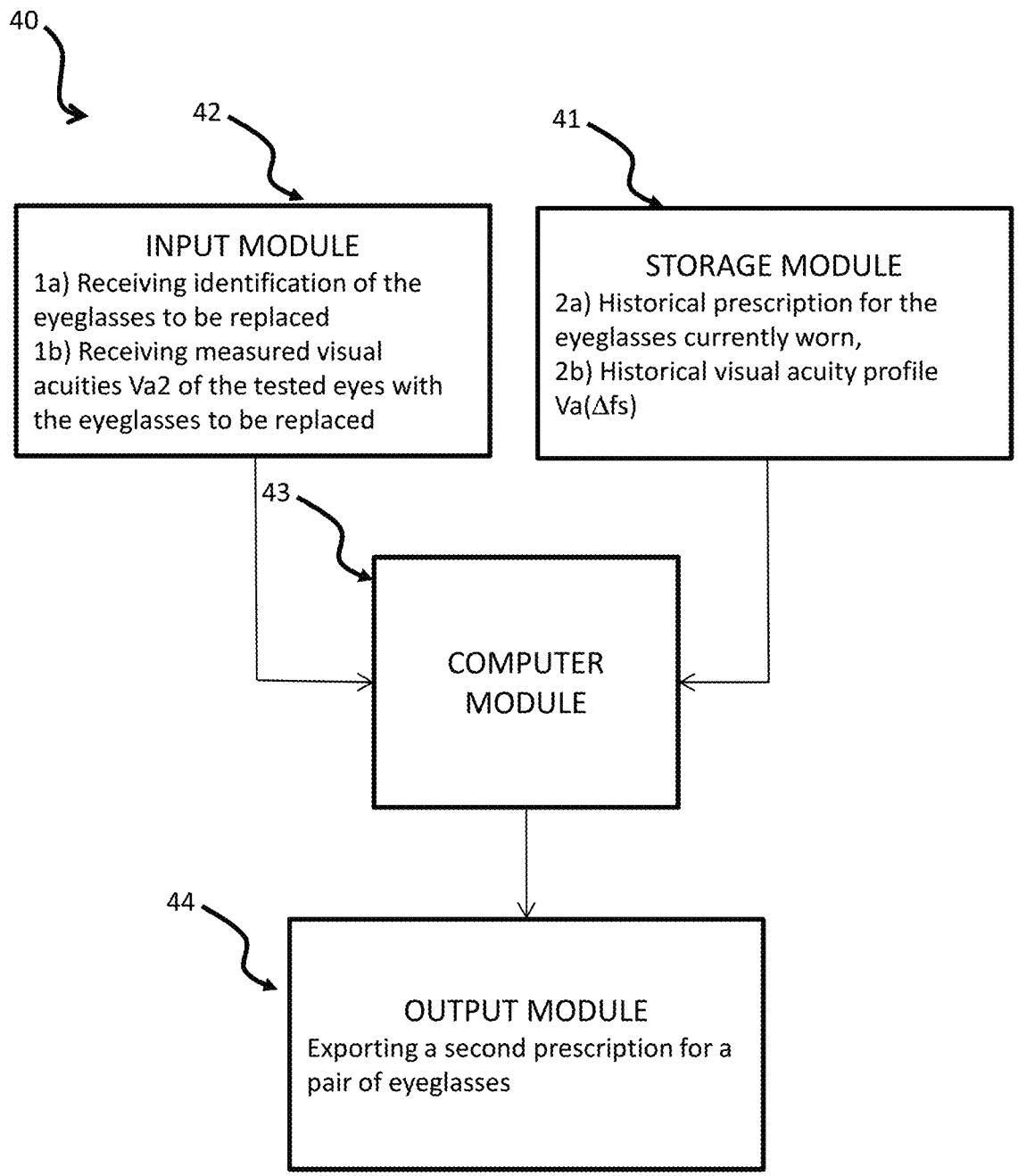
FIG. 4 shows a block diagram for a system for generating a refractive prescription, in accordance with some embodiments.

In still another embodiment, FIG. 4 shows a block diagram of a system 40 for producing a refractive prescription of corrective lenses, such as an updated prescription of a new pair of eyeglasses. The prescription is based on acuity measured with eyeglasses worn currently by the test subject and a historical prescription, as well as a historical acuity profile saved in a record. The system 40 includes a database or storage module 41 for storing historical data with the eyeglass worn currently. The storage module 41 may be, for example, an electronic device having memory capability, such as a computer database. In other embodiments the storage module 41 may be a repository of written records. The historical data includes 2a) a first prescription for the first pair of corrective lenses, which are the eyeglasses currently worn, where prescription values in the first prescription include a spherical power fs1, and if applicable, a cylinder power fc1 and a cylinder angle fa1; and 2b) a historical visual acuity profile Va($\Delta$fs) that describes a relationship between a measured visual acuity Va(i) and a variation in spherical power $\Delta$fs(i), the historical visual acuity profile Va($\Delta$fs) being measured at a first time point. The historical visual acuity profile is collected by measuring a plurality of visual acuities Va(1), Va(2) . . . Va(i) of the tested eyes with the historical (first) prescription while varying the focus power for each eye, the variation in focus power being $\Delta$fs(1), $\Delta$fs(2) . . . $\Delta$fs(i).

The system 40 also includes an input module 42 for receiving information for the tested subject. The input module 42 can be, for example, a computer hardware device that can receive electronic data, or receive information obtained from written records. The information received includes: 1a) identification information of the eyeglasses to be replaced, such as eyeglasses worn currently by the test subject. The identification information may be assigned by the eyeglass vendor who provided the eyeglasses. In some embodiments the information can be 1a) an existing prescription with the tested subject. The received information by the input module 42 also includes 1b) a second visual acuity Va2 of the eyes of the tested subject, the second visual acuity Va2 being measured using the first prescription at a second time point. Alternatively, the second visual acuity Va2 may be measured using the first pair of corrective lenses according to the first prescription. The second visual acuity Va2 is up-to-date tested visual acuity VAc for each eye of the tested subject with the eyeglasses worn currently, such as visual acuities measured at home using the eyeglasses to be replaced.

System 40 also includes a computer module 43 for 3a) retrieving information, such as the first prescription, from the storage module 41; 3b) receiving information from the input module 42, 3c) computing a new spherical power for each eye of the tested subject based on data from the input module 42 and the storage module 41, such as the historical visual acuity profile Va($\Delta$fs) and the second visual acuity Va2; and 3d) generating a second prescription for a second pair of corrective lenses based on the first prescription and the computed new spherical power for each eye. The computer module 43 may be, for example, a computer hardware processor having computing capability and appropriate software to process data and perform computations. An output module 44 exports the generated second prescription for the new, second pair of eyeglasses, such as exporting the second prescription to a lens vendor or to the tested subject. In some embodiments, the output module 44 is further configured for ordering the new, second pair of eyeglasses based on the generated second prescription, and delivering the new eyeglasses to the consumer. The output module 44 may be, for example, a computer hardware device and/or a software program having capability for information processing.

In some embodiments for the system 40 of FIG. 4, the first prescription is based on measurements of refractive errors of the eyes of the tested subject, measured using a refraction device at the first time point by an optical professional at an optical office. Also, the second visual acuity Va2 measured at the second time point is self-administered by the tested subject at a different location from the optical office. For instance, the tested subject may perform the second visual Acuity Va2 measurement at their home, a community center, or other non-medical facility.

In some embodiments the storage module 41, the input module 42, the computer module 43 and the output module 44 of system 40 in FIG. 4 are further configured as a web-based, a cloud-based, or a remote system. In such embodiments the input module 42 is configured to receive electronic records from a personal electronic device of the tested subject or to allow an operator to enter data provided by the tested subject. In embodiments of a web-based or cloud-based system, the storage module 41, the input module 42, the computer module 43 and the output module 44 are all in electronic communication with each other. In some embodiments, one or more modules of system 40 may be on the same computer hardware device. In some embodiments, the system 40 is accessible remotely by users such as the consumer and by optical offices, where access is obtained through, for example, a computer workstation, personal computer, a laptop, a tablet, a smart phone, or a smart watch.

Figure 5:
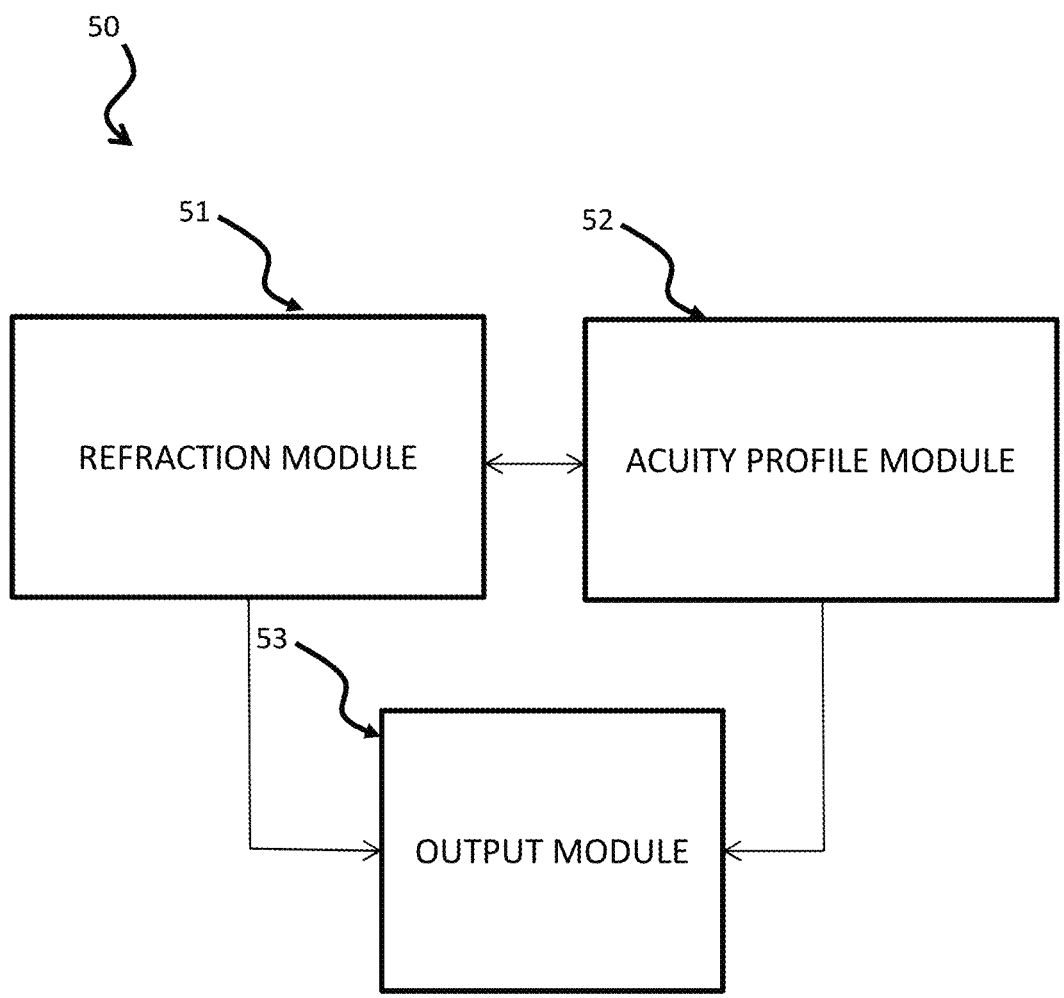
FIG. 5 shows a block diagram for a refraction system used in generating a refractive prescription, in accordance with some embodiments.

In yet another embodiment, FIG. 5 shows a block diagram of a refraction system 50 for producing a refractive prescription of corrective lenses. The refraction system 50 includes a refraction module 51, an acuity profile module 52 and an output module 53. The refraction module 51 is configured to measure refractive errors in left and right eyes of a tested subject and generate a prescription for a pair of corrective lenses with which both left and right eyes of the tested subject are corrected for the best vision performance. The prescription for a pair of corrective lenses, such as eyeglasses or contact lenses, includes at least a spherical power, and possibly a cylinder power and a cylinder angle if applicable, such as if the cylinder power and cylinder angle affect the prescription. In one embodiment, the refraction module 51 further includes an aberrometer, and the prescription for a pair of corrective lenses further includes a spherical aberration or coma. In some embodiments the refraction module 51 includes a phoropter, the phoropter having the spherical power setting used for measuring the plurality of visual acuities.

The refraction system 50 also includes an acuity profile module 52 configured to measure and record a plurality of visual acuities of the left and right eyes of the tested subject as a function of spherical power. The acuity profile module 52 may include, for example, a phoropter having multiple spherical power settings, and/or an acuity chart having letters or other objects for the tested subject to visually identify (e.g., Snellen Chart, Tumbling C chart, and other types of acuity charts). The measuring of visual acuities involves changing a spherical power setting (i.e., value) in the refraction module 53 and recording each visual acuity at each spherical power setting based on feedback of the tested subject. The visual acuities measured at each spherical power setting form an acuity profile. The refraction system 50 also includes an output module 53 is configured for printing, displaying, and exporting the generated prescription for a pair of corrective lenses. The output module 53 also is configured for printing, displaying, and exporting the acuity profile. The output module 53 may be, for example, a computer station with a monitor and printer. The refraction system 50 may also be further configured to be web-connected or cloud-connected. For example, the refraction system 50 may be electronically connected to the system 40 of FIG. 4 to provide refraction and prescription information to the storage module 41 and/or input module 42.

Figure 6:
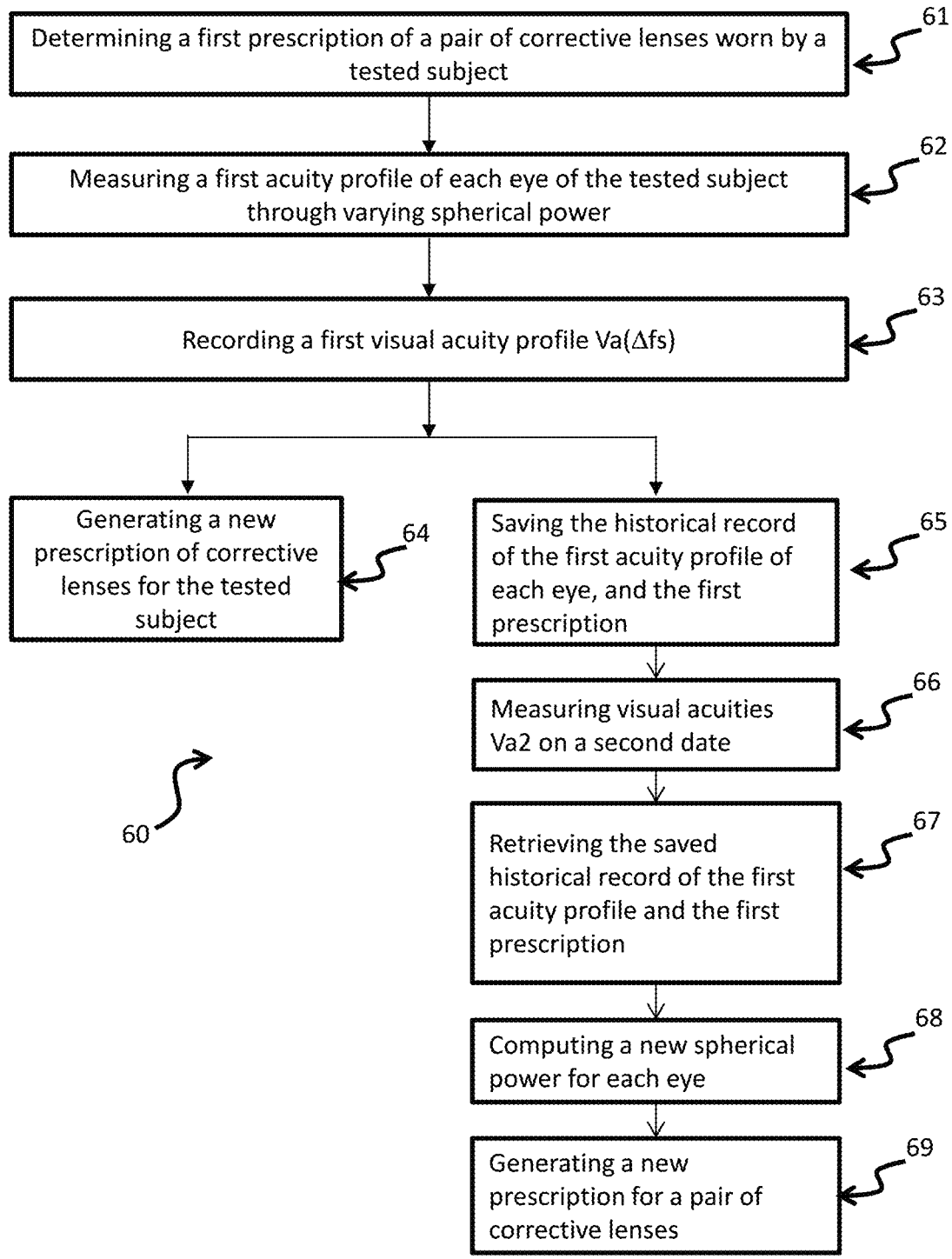
FIG. 6 shows a flow chart of a method for producing a refractive prescription for human eyes, when access to historical records from when a pair corrective lenses was prescribed is not available, in accordance with some embodiments.

In still another embodiment, FIG. 6 shows a flow chart 60 of another method for producing a refractive prescription of eyeglasses for human eyes after a pair of eyeglasses is made, but without historical records from when the eyeglasses were prescribed. In step 61, a first prescription of a pair of corrective lenses (e.g., eyeglasses or contact lenses) worn by a tested subject at a first time point is determined from a record of a previous prescription or by using a lensometer to measure the first pair of corrective lenses. The first prescription includes at least a spherical power fs1, and if applicable, a cylinder angle fc1 and a cylinder angle fa1.

In step 62, a first visual acuity profile of each eye of the tested subject at the first time point is measured. The first visual acuity profile is measured through focus; that is, by using varying values of focus power (spherical power). The first acuity profile includes a plurality of measured visual acuities Va(i), each measured visual acuity Va(i) being taken at each spherical power value. The measurements can be achieved using the first prescription with a plurality of variations in spherical power Δfs(i). For example, the tested subject have the visual acuity measurements performed using first pair of corrective lenses and through optical components that allow the spherical power Δfs to be varied. That is, the optical components, such as lenses on a phoropter, or individual spherical power lenses, allow for changing the spherical power for a plurality of settings. In other embodiments, the measured visual acuity Va(i) can be achieved through a system that can provide refractive powers according to the first prescription and allow the spherical power Δfs to be varied through a plurality of values. The spherical power for a plurality of values or settings is represented by Δfs(1), Δfs(2) . . . Δfs(i). A historical visual acuity profile Va(Δfs) can thus be obtained that describes the relationship between measured visual acuity Va(i) and the variation in spherical power Δfs(i).

The first visual acuity profile, which may also be considered as a historical visual acuity profile, is recorded in step 63. the first visual acuity profile Va(Δfs) describes a relationship between the measured visual acuities Va(i) and the variation in spherical power Δfs(i). A new prescription of a new pair of corrective lenses for the tested subject is generated if necessary in step 64, when the tested subject's vision has changed enough to require a new prescription. The new prescription is generated at a second time point later than the first time point, using the first visual acuity profile Va(Δfs). For generating the prescription of a new pair of corrective lenses, the new prescription of eyeglasses for the tested subject is generated by determining a spherical power adjustment Δfs to the spherical power fs1.

The historical visual acuity profile may be utilized for generating a prescription at a future date. In step 65, a historical record of the first acuity profile of each eye of the tested subject as well as the determined first prescription of the eyeglasses worn by the tested subject are saved in a record for generating a new prescription of eyeglasses in the future.

In one embodiment, generating a new prescription of eyeglasses in the future in FIG. 6 further comprises measuring visual acuities Va2 of the tested eyes with the eyeglasses according to the first prescription at a second time point (step 66); and retrieving the saved historical record of the first acuity profile Va(Δfs) of each eye of the tested subject, as well as retrieving the first prescription of the eyeglasses worn by the tested subjects (step 67). The new prescription includes at least a focus error, and possibly a cylinder angle and a cylinder angle. The method of FIG. 6 also includes computing a new spherical power for each eye (step 68) based on the recorded first visual acuity profile Va($\Delta$fs) and the measured second visual acuities Va2 on the second time point. In step 69, a new prescription of a pair of corrective lenses is generated based on the first prescription for the first (previously worn) pair of corrective lenses and the computed new spherical power for each eye.

Measuring visual acuities Va of the tested eyes with the eyeglasses worn by the tested subject in FIG. 6, such as at steps 62 and 66, can be self-administered by the tested subject at a location other than at an optical office, such as, but not limited to, at home of the tested subject. In other embodiments, a non-optically trained person can assist the tested subject in measuring the visual acuities Va at a location outside of a professional optical office. In some embodiments, measuring the second visual acuity Va2 includes using a test acuity chart placed at a plurality of distances from the tested subject and determining an add-on spherical power for a presbyopia correction.

The method of FIG. 6 may be further configured into a web-based system, a cloud-based system, or a remote system. For example, recording of the first visual acuity profile, retrieving of the first visual acuity profile and computing of the new prescription of corrective lenses is performed on a web-based, cloud-based system.

In yet further embodiments, a method or an information processing method for updating prescription of corrective lenses, such as eyeglasses or contact lenses, uses a conventional method in an optical office for a first pair of corrective lenses to generate an updated prescription at a later date, without the need for an office visit. The method includes obtaining a first pair of corrective lenses for a tested subject in an optical office such as an eyeglass shop using a conventional method. The following information is collected at the optical office: a) the first prescription of the first pair of corrective lenses, and b) vision performance such as visual acuity of the tested eyes for the prescribed corrective lenses. For example, the vision performance of the eyes may be measured with the first pair of corrective lenses plus a plurality of variations in spherical power $\Delta$fs(i). The conventional method used to collect the information is performed at a first time point, and may utilize steps as described in steps 11-13 of FIG. 1 and the refraction system 50 of FIG. 5.

At a second time point, visual performance such as a visual acuity Va2 of the eyes is collected with the first pair of corrective lenses by a non-optically trained person at a location away from any optical office, such as away from the original optical office that was visited or any other optical office. Collecting visual performance such as the second visual acuity Va2 of the tested eyes with the first pair of eyeglasses is performed for a plurality of focus settings (e.g., variations in spherical power $\Delta$fs(i)) by, in some embodiments, measuring acuity through lenses that provide the variations in focus settings and through the first pair of eyeglasses. In other embodiments, the second visual acuity Va2 is collected by placing an acuity chart at a plurality of distances and having the tested subject read the acuity chart. The visual acuity Va2 may be measured according to, for example, step 16 of FIG. 1. A change in spherical power from the first time point to the second time point is determined, such as according to step 18 of FIG. 1. A second prescription for a second pair of corrective lenses is generated based on the information collected at the original optical office and the visual performance collected with the first pair of corrective lenses away from the original optical office. For example, the second prescription may be generated as described in step 19 of FIG. 1.

In one embodiment, the method further includes ordering and delivering the new (second) pair of corrective lenses according to the second prescription that was generated, such as described in step 20 of FIG. 1. In some embodiments, the method can be configured for operation on a web-based system, or even a cloud-based system. For example, the collecting of the visual acuity Va2 may be recorded and stored on a web-based or cloud-based system. The determination of the change in spherical power from the first time point to the second time point, as well as the generating of the second prescription may be computed and output on the web-based or cloud-based system using information (e.g., visual acuity records and the first prescription) stored or accessed by the system. In some embodiments, the tested subject can verify performance of the second pair of corrective lenses once the second pair of corrective lenses is delivered.

In other embodiments, a method or information processing method for updating a prescription of corrective lenses uses a first prescription from conventional methods in an optical office to generate an updated new prescription without the need for an office visit. The method includes using a conventional method in an optical office to obtain a first pair of corrective lenses for eyes of a tested subject. Information is collected at the optical office, including a) the first prescription of the first pair of corrective lenses, and b) a first visual performance of the eyes, the first visual performance comprising a visual acuity profile Va($\Delta$fs) of the eyes with the first pair of corrective lenses. The conventional method uses a refraction device to measure refractive errors of both left and right eyes of the tested subject, for example as described in step 11 of FIG. 1. A second visual performance of the eyes is collected, such as a second visual acuity Va2 with the first pair of corrective lenses by self-administration away from any optical office, for example as described in step 16 of FIG. 1. The collecting of the second visual performance is performed for a plurality of variations in spherical power $\Delta$fs(i) by i) measuring acuity through lenses and the first pair of corrective lenses or ii) placing acuity chart at a plurality of distances. A new prescription for a new pair of corrective lenses is generated based on the information collected at the optical office and the second visual performance that was collected with the first pair of corrective lenses away from any optical office, such as described in relation to step 19 of FIG. 1. The methods may include ordering and delivering the new pair of corrective lenses according to the new prescription, as described in relation to step 20 of FIG. 1. The methods may also include verifying, by the tested subject, a performance of the new pair of corrective lenses once the new pair of corrective lenses is delivered. In some embodiments, the collecting and generating are performed using a web-based system or a cloud-based system.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the spirit and scope of the present invention, which is more particularly set forth in the appended claims. Furthermore, those skilled in the art will appreciate that the foregoing description is by way of example only, and is not intended to limit the invention.

What is claimed is:

1. A method for producing a refractive prescription for human eyes, the method comprising:
    using a refraction device to obtain measured refractive errors of eyes of a tested subject at a first time point;
    generating a first prescription for a first pair of corrective lenses according to the measured refractive errors, wherein the first prescription comprises a spherical power fs1, a cylinder power fc1 and a cylinder angle fa1;
    measuring, at the first time point, a historical visual acuity profile Va(Δfs) of the eyes of the tested subject, wherein the historical visual acuity profile Va(Δfs) comprises a plurality of visual acuities Va(i) measured using the first prescription with a plurality of variations in spherical power Δfs(i) of the spherical power fs1 of the first prescription;
    recording the historical visual acuity profile Va(Δfs) and data on the first prescription;
    measuring, at a second time point, a second visual acuity Va2 of the eyes of the tested subject using the first pair of corrective lenses according to the first prescription;
    computing a new spherical power fs2 for the eyes of the tested subject using the historical visual acuity profile Va(Δfs) and the second visual acuity Va2; and
    generating a second prescription for a second pair of corrective lenses based on the first prescription and the new spherical power fs2 for the eyes, the second prescription comprising the new spherical power fs2, the cylinder power fc1 and the cylinder angle fa1.

2. The method of claim 1, wherein:
    the using a refraction device at the first time point is administered by an optical professional at a first optical office; and
    the measuring at the second time point is administrated by a non-optically trained person at a location away from an optical office.

3. The method of claim 2, wherein the measuring at the second time point is self-administered by the tested subject at a home of the tested subject.

4. The method of claim 1, further comprising producing the first pair of corrective lenses according to the first prescription.

5. The method of claim 1, further comprising providing a web-based system or a cloud-based system, wherein:
    the recording comprises storing the historical visual acuity profile Va(Δfs) on the web-based system or the cloud-based system; and
    the computing comprises retrieving the historical visual acuity profile Va(Δfs) from the web-based system or the cloud-based system.

6. The method of claim 1, wherein:
    the using the refraction device comprises:
        measuring aberrations in the eyes with objective measurements from an aberrometer, the objective measurements comprising the cylinder power fc1 and the cylinder angle fa1; and
        measuring the spherical power fs1 of the eyes with subjective responses from the tested subject; and
    the measured refractive errors in the generating the first prescription comprises the cylinder power fc1, the cylinder angle fa1, and the spherical power fs1 for each eye.

7. The method of claim 6, wherein the first prescription further comprises a correction for spherical aberration or coma.

8. The method of claim 1, wherein the measuring of the second visual acuity Va2 at the second time point is performed under a controlled environment, the controlled environment including at least one of the group consisting of: light conditions, type of acuity chart, and distance from the acuity chart to the tested subject.

9. The method of claim 1, wherein the measuring of the second visual acuity Va2 comprises:
    placing an acuity chart at a plurality of distances from the tested subject; and
    determining an add-on spherical power for a presbyopia correction.

10. The method of claim 1, further comprising ordering and delivering the second pair of corrective lenses according to the second prescription.

11. The method of claim 1, further comprising verifying, by the tested subject, a performance of the second pair of corrective lenses.

12. The method of claim 1, wherein the first pair of corrective lenses or the second pair of corrective lenses are eyeglasses or contact lenses.

13. A method for updating a refractive prescription for human eyes, the method comprising:
    receiving current information of eyes of a tested subject, the current information comprising a) identification information of current corrective lenses of the tested subject, the identification information assigned at a first location, and b) a current visual acuity VAc for each eye of the tested subject with the current corrective lenses, the current visual acuity VAc being assessed at a second location;
    using the identification information of the current corrective lenses to retrieve historical data, wherein the historical data includes: i) a historical prescription comprising a spherical power fs1 for the current corrective lenses, a cylinder power fc1 and a cylinder angle fa1; and ii) a historical visual acuity profile Va(Δfs) describing a relationship between a plurality of measured visual acuities Va(i) and a plurality of variations in spherical power Δfs(i) on top of the historical prescription;
    computing a new spherical power fs2 based on the current visual acuity VAc and the historical visual acuity profile Va(Δfs); and
    generating a new prescription for a new pair of corrective lenses, wherein the new prescription includes the new spherical power fs2, the cylinder power fc1 and the cylinder angle fa1.

14. The method of claim 13, wherein the identification information is assigned by a lens vendor at the first location, and wherein the second location is different from the first location.

15. The method of claim 13 wherein the cylinder power fc1 and the cylinder angle fa1 are measured by an aberrometer.

16. The method of claim 13 wherein the historical prescription includes spherical aberration or coma.

17. The method of claim 13 further comprising providing a web-based system or a cloud-based system, the web-based system or the cloud-based system being accessible by a personal electronic device of the tested subject and comprising:
    an input module configured to receive the current information of the eyes of the tested subject;

a storage module configured to store the historical data; and a computer module configured to compute the new spherical power fs2 and to generate the new prescription using the historical data stored on the storage module.

18. The method of claim 13, wherein the current visual acuity VAc comprises a plurality of visual acuities measured with a test acuity chart placed at a plurality of distances for determining an add-on spherical power for a presbyopia correction.

19. The method of claim 13, further comprising ordering and delivering the new pair of corrective lenses based on the new prescription.

20. The method of claim 19, further comprising accepting payment information from the tested subject for the ordering of the new pair of corrective lenses.

21. The method of claim 19 wherein the new pair of corrective lenses are eyeglasses, and the ordering comprises offering to and receiving from the tested subject a frame style for the new pair of corrective lenses.

22. A system for producing a refractive prescription of corrective lenses for eyes of a tested subject, comprising:
a storage module configured to store I) a first prescription for a first pair of corrective lenses, wherein the first prescription comprises a spherical power fs1, a cylinder power fc1 and a cylinder angle fa1, and II) a historical visual acuity profile Va($\Delta$fs) that describes a relationship between a measured visual acuity Va(i) and a variation in spherical power $\Delta$fs(i), the historical visual acuity profile Va($\Delta$fs) being measured at a first time point;
an input module configured to receive a second visual acuity Va2 of the eyes of the tested subject, the second visual acuity Va2 being measured at a second time point using the first prescription or the first pair of corrective lenses according to the first prescription;
a computer module configured to a) retrieve the first prescription from the storage module, b) receive information from the input module; c) compute a new spherical power for each eye of the tested subject based on the historical visual acuity profile Va($\Delta$fs) and the second visual acuity Va2, and c) generate a second prescription for a second pair of corrective lenses based on the first prescription and the computed new spherical power for each eye; and
an output module configured to export the second prescription.

23. The system of claim 22, wherein:
the first prescription is based on measurements of refractive errors of the eyes of the tested subject, measured using a refraction device at the first time point by an optical professional at an optical office; and
the second visual acuity Va2 measured at the second time point is self-administered by the tested subject at a different location from the optical office.

24. The system of claim 22, wherein:
the storage module, the input module, the computer module and the output module are configured as a web-based or a cloud-based system; and
the input module is configured to receive electronic records from a personal electronic device of the tested subject or to allow an operator to enter data provided by the tested subject.

25. A refraction system for producing a refractive prescription of corrective lenses, comprising:
a refraction module configured to measure refractive errors in left and right eyes of a tested subject and to generate a prescription for a pair of corrective lenses with which both left and right eyes of the tested subject are corrected for best vision performance;
an acuity profile module configured to measure and record a plurality of visual acuities of the left and right eyes of the tested subject as a function of spherical power, the measuring comprising changing a spherical power setting in the refraction module and recording each visual acuity at each spherical power setting based on feedback of the tested subject, wherein an acuity profile comprises the plurality of visual acuities; and
an output module configured for 1) printing, displaying, and exporting the generated prescription for the pair of corrective lenses, and 2) printing, displaying, and exporting the acuity profile.

26. The refraction system of claim 25, wherein the generated prescription for the pair of corrective lenses includes a first spherical power fs1, a cylinder power fc1 and a cylinder angle fa1.

27. The refraction system of claim 25, wherein the refraction module comprises an aberrometer, and wherein the generated prescription for the pair of corrective lenses further includes a spherical aberration or coma.

28. The refraction system of claim 25, wherein the refraction module comprises a phoropter, the phoropter comprising the spherical power setting used for measuring the plurality of visual acuities.

29. A method for producing a refractive prescription of corrective lenses, the method comprising:
determining, at a first time point, a first prescription of a first pair of corrective lenses worn by a tested subject, the determining being based on a record of a previous prescription or using a lensometer to measure the first pair of corrective lenses, wherein the first prescription includes a spherical power fs1, a cylinder power fc1 and a cylinder angle fa1;
measuring a first visual acuity profile Va($\Delta$fs) of each eye of the tested subject at the first time point, the first visual acuity profile Va($\Delta$fs) comprising a plurality of visual acuities Va(i) measured using the first prescription with a plurality of variations in spherical power $\Delta$fs(i);
recording the first visual acuity profile Va($\Delta$fs) that describes a relationship between the measured plurality of visual acuities Va(i) and the variations in spherical power $\Delta$fs(i); and
generating a new prescription of corrective lenses for the tested subject at a second time point later than the first time point, using the first visual acuity profile Va($\Delta$fs).

30. The method of claim 29, wherein the generating a new prescription of corrective lenses for the tested subject comprises determining a spherical power adjustment $\Delta$fs2 to the spherical power fs1.

31. The method of claim 29, wherein the generating a new prescription at the second time point further comprises:
measuring a second visual acuity Va2 of the eyes of the tested subject using the first pair of corrective lenses at the second time point;
retrieving the first visual acuity profile Va($\Delta$fs) and the determined first prescription;
computing a new spherical power for each eye based on the first visual acuity profile Va($\Delta$fs) and the second visual acuity Va2; and
generating the new prescription of corrective lenses using the first visual acuity profile Va($\Delta$fs), the first prescription for the first pair of corrective lenses, and the computed new spherical power for each eye.

32. The method of claim 31 wherein the measuring of the second visual acuity Va2 at the second time point is self-administrated by the tested subject at a location other than an optical office.

33. The method of claim 31 wherein the measuring of the second visual acuity Va2 comprises:
   using a test acuity chart placed at a plurality of distances from the tested subject; and
   determining an add-on spherical power for a presbyopia correction.

34. The method of claim 31 wherein the recording of the first visual acuity profile Va(Δfs), the retrieving of the first visual acuity profile Va(Δfs) and the generating of the new prescription of corrective lenses is performed on a web-based system or a cloud-based system.

35. A method for updating a prescription of corrective lenses, the method comprising:
   using, at a first time point, a refraction device in an optical office to obtain a first pair of corrective lenses for eyes of a tested subject with the following information collected: a) a first prescription of the first pair of corrective lenses, and b) vision performance of the eyes that is measured with the first pair of corrective lenses plus a plurality of variations in spherical power Δfs(i);
   collecting, at a second time point, a visual acuity Va2 of the eyes with the first pair of corrective lenses by non-optically trained person at a location away from any optical office when a second pair of corrective lenses is ordered away from any optical office;
   determining a change in spherical power of each eye from the first time point to the second time point; and
   generating a second prescription for the second pair of corrective lenses based on the information collected at the optical office and the visual acuity Va2.

36. The method of claim 35, further comprising ordering and delivering the second pair of corrective lenses according to the second prescription.

37. The method of claim 35 wherein the collecting, the determining and the generating are performed using a web-based system or a cloud-based system.

38. The method of claim 35, further comprising verifying, by the tested subject, a performance of the second pair of corrective lenses.

39. A method for updating a prescription of corrective lenses, the method comprising:
   using a refraction device in an optical office to obtain a first pair of corrective lenses for eyes of a tested subject with the following information collected:
   a) a first prescription of the first pair of corrective lenses, and b) a first visual performance of the eyes, the first visual performance comprising a visual acuity profile Va(Δfs) of the eyes with the first pair of corrective lenses, wherein the refraction device is used to measure refractive errors of both left and right eyes of the tested subject;
   collecting a second visual performance of the eyes comprising a second visual acuity Va2 with the first pair of corrective lenses by self-administration away from any optical office, wherein the collecting of the second visual performance is performed for a plurality of variations in spherical power Δfs(i) by i) measuring acuity through lenses and the first pair of corrective lenses or ii) placing an acuity chart at a plurality of distances; and
   generating a new prescription for a new pair of corrective lenses based on the information collected at the optical office and the second visual performance collected with the first pair of corrective lenses away from any optical office.

40. The method of claim 39, further comprising ordering and delivering the new pair of corrective lenses according to the new prescription.

41. The method of claim 40 further comprising verifying, by the tested subject, a performance of the new pair of corrective lenses once the new pair of corrective lenses is delivered.

42. The method of claim 39 wherein the collecting and generating are performed using a web-based system or a cloud-based system.

* * * * *